US009839568B2

(12) United States Patent
Butler

(10) Patent No.: US 9,839,568 B2
(45) Date of Patent: Dec. 12, 2017

(54) SWING WALKER

(71) Applicant: Barry A. Butler, Owatonna, MN (US)

(72) Inventor: Barry A. Butler, Owatonna, MN (US)

( * ) Notice: Subject to any disclaimer, the term of this patent is extended or adjusted under 35 U.S.C. 154(b) by 0 days.

(21) Appl. No.: 15/180,690

(22) Filed: Jun. 13, 2016

(65) Prior Publication Data
US 2016/0279014 A1 Sep. 29, 2016

Related U.S. Application Data

(63) Continuation of application No. 13/800,767, filed on Mar. 13, 2013, now Pat. No. 9,364,383.

(60) Provisional application No. 61/707,304, filed on Sep. 28, 2012.

(51) Int. Cl.
*A61H 3/00* (2006.01)
*A61H 3/02* (2006.01)
*A61F 5/01* (2006.01)

(52) U.S. Cl.
CPC ............ *A61H 3/00* (2013.01); *A61F 5/0195* (2013.01); *A61H 3/02* (2013.01); *A61H 2003/005* (2013.01); *A61H 2003/007* (2013.01); *A61H 2003/0211* (2013.01)

(58) Field of Classification Search
CPC ........ A61H 2003/005; A61H 2003/007; A61H 3/00; A61F 5/0111; A61F 5/0195; A61F 5/0127
USPC .............. 36/125; 602/23, 26, 27, 28; 135/65
See application file for complete search history.

(56) References Cited

U.S. PATENT DOCUMENTS

| 1,607,834 A | 11/1926 | Line |
| 1,660,721 A * | 2/1928 | Schrag ................. A61F 5/0102 602/16 |
| 2,264,570 A | 12/1941 | Holden |
| 2,423,354 A | 7/1947 | Van Hoesen |
| 2,585,730 A * | 2/1952 | Bodnar .................... A61H 3/00 135/68 |
| 2,796,916 A * | 6/1957 | Womble ................... A61H 3/00 135/67 |
| 3,780,728 A | 12/1973 | Stader |
| 4,252,112 A | 2/1981 | Joyce |

(Continued)

FOREIGN PATENT DOCUMENTS

| DE | 10057286 | 3/2006 |
| WO | WO 97-49359 | 1/1997 |

OTHER PUBLICATIONS

International Search Report and Written Opinion issued by the U.S. Receiving Office, regarding corresponding International patent application Serial No. PCT/US2013/062093; dated Mar. 18, 2014; 7 pages.

*Primary Examiner* — Noah Chandler Hawk
(74) *Attorney, Agent, or Firm* — Fox Rothschild LLP

(57) ABSTRACT

A suspension walker which may be weighted or unweighted is provided. The suspension walker includes a sole plate having a rocker bottom, a yoke portion and an extension leg attached to the yoke portion. A boot received by a patient's foot is operably coupled to the yoke portion by a first fastener and to an upper portion of the extension leg by a second fastener. An extension leg may be operably coupled at a hinge axis to an upper hinged portion. The hinge axis is configured to be aligned with the knee. A below the knee collar operably and securely couples the boot to the extension leg and the yoke portion. An above the knee collar operably secures the upper hinged portion to the patient's thigh.

4 Claims, 9 Drawing Sheets

(56) References Cited

U.S. PATENT DOCUMENTS

| | | | |
|---|---|---|---|
| 4,641,639 A | | 2/1987 | Padilla |
| 5,165,436 A | * | 11/1992 | Hall, Sr. .................. A61H 3/02 |
| | | | 135/66 |
| 5,178,595 A | | 1/1993 | MacGregor |
| 5,183,036 A | | 2/1993 | Spademan |
| 5,368,551 A | | 11/1994 | Zuckerman |
| 5,620,411 A | | 4/1997 | Schumann et al. |
| 5,993,404 A | | 11/1999 | McNiel |
| 6,464,659 B1 | | 10/2002 | DeToro et al. |
| 6,976,972 B2 | | 12/2005 | Bradshaw |
| 6,991,613 B2 | | 1/2006 | Sensabaugh |
| 6,997,891 B1 | | 2/2006 | Vecsey |
| 7,270,644 B2 | | 9/2007 | Ingimundarson |
| 7,294,114 B1 | | 11/2007 | Clement et al. |
| 7,418,755 B2 | | 9/2008 | Bledsoe |
| 7,597,674 B2 | | 10/2009 | Hu et al. |
| 7,743,532 B2 | | 6/2010 | Bledsoe et al. |
| 7,896,826 B2 | | 3/2011 | Hu et al. |
| 7,963,932 B2 | * | 6/2011 | Ashihara ............... A61F 5/0102 |
| | | | 601/35 |
| 8,021,316 B2 | | 9/2011 | Franke et al. |
| 9,168,166 B2 | | 10/2015 | Bradshaw |
| 9,375,377 B1 | * | 6/2016 | Edwards .................. A61H 3/00 |
| 2002/0128574 A1 | | 9/2002 | Darby |
| 2004/0187355 A1 | | 9/2004 | Mahoney et al. |
| 2005/0131324 A1 | | 6/2005 | Bledsoe |
| 2005/0145256 A1 | | 7/2005 | Howard et al. |
| 2009/0227927 A1 | | 9/2009 | Frazer |
| 2009/0306565 A1 | | 12/2009 | Chan |
| 2010/0106065 A1 | | 4/2010 | Ward |
| 2012/0035520 A1 | | 2/2012 | Ingimundarson et al. |
| 2013/0046222 A1 | | 2/2013 | Gizzi |
| 2013/0152986 A1 | | 6/2013 | Hunter |

* cited by examiner

SWING WALKER

RELATED APPLICATION DATA

This application is a continuation of U.S. patent application Ser. No. 13/800,767, now allowed, filed Mar. 13, 2013; which claims priority to U.S. application Ser. No. 61/707,304, filed on Sep. 28, 2012, the entireties of which are incorporated herein by reference.

FIELD OF THE INVENTION

This invention relates to the field of swing or suspension walkers and more particularly to a device and method that decreases the impact forces to which a patient's foot is subjected if walking in a cast or boot after surgery or other injury.

BACKGROUND OF THE INVENTION

Walking and running can be defined as methods of locomotion involving the use of the two legs, alternatively, to provide both support and propulsion, with at least one foot being in contact with the ground at all times. While the terms gait and walking are often used interchangeably, the word gait refers to the manner or style of walking, rather than the actual walking process. The gait cycle is the time interval between the exact same repetitive events of walking.

The defined cycle can start at any moment, but it typically begins when one foot contacts the ground and ends when that foot contacts the ground again. If it starts with the right foot contacting the ground, then the cycle ends when the right foot makes contact again. Thus, each cycle begins at initial contact with a stance phase and proceeds through a swing phase until the cycle ends with the limb's next initial contact. Stance phase accounts for approximately 60 percent, and swing phase for approximately 40 percent, of a single gait cycle.

However following injury or surgery to the foot, a patient may be fitted with a walker to assist in locomotion. Various devices that allow a patient to continue the normal gait cycle are known, for example casts, braces, cuffs, splints, soft boots, hard boots and the like, which are designed to protect and stabilize the foot following injury or surgery. However, most of these devices are constructed such that the patient's foot is still subjected to all the impact force when it hits the ground. Hard surfaces in modern human environments have changed the forces encountered by the human musculoskeletal system during the gait cycle as compared to the forces which it evolved to sustain. Impact energies from such surfaces enter the body through boney and dense tissues and through soft and fatty tissues. When a patient is trying to recover from injury or surgery, such impact energy frequently exacerbates the injury.

Other causes of injury to the foot relate to underlying pathological disease states, such as by way of example, diabetes. Diabetes is a chronic disease that affects up to six percent of the population in the U.S. and is associated with progressive disease of the microvasculature. Complications from diabetes include not only heart disease, stroke, high blood pressure, diabetic retinopathy but also in particular diabetic neuropathic foot disease.

Diabetic neuropathic foot disease typically results in the formation of ulcers which commonly result from a break in the barrier between the dermis of the skin and the subcutaneous fat that cushions the foot during ambulation. This rupture may lead to increase pressure on the dermis. In order for the ulcer to heal, the patient must either stay off their feet altogether or use a pressure relieving orthotic or brace.

While there are devices and methods that purport to prevent planar ulcer formation in a diabetic patient there are no devices on the market that treat the ulcer with dynamic offloading of the weight bearing limb.

Therefore, what is needed is a system and method that can be used to mitigate excessive impact forces on an injured foot during locomotion or off-load an injured, weight bearing limb during locomotion while allowing a patient to maintain normal gait function.

BRIEF SUMMARY OF THE INVENTION

The aforementioned problems are addressed by the weighted and unweighted systems and method in accordance with the invention. In one aspect of the present invention, the system broadly includes a sole plate having a rocker bottom, a yoke portion and an extension leg attached to the yoke portion. A boot received by a patient's foot is operably coupled to the yoke portion by a first fastener and to an upper portion of the extension leg by a second fastener.

In another aspect of the invention, the extension leg may be operably coupled at a hinge axis to an upper hinged portion. The hinge axis is aligned with the knee. A below the knee collar operably and securely couples the boot to the extension leg and the yoke portion. An above the knee collar operably secures the upper hinged portion to the patient's thigh.

In another aspect of the invention a patellar suspension may operably couple the boot to the extension leg and the patient's leg.

The foregoing elements work together as a system to off-load an injured, weight bearing limb during locomotion and mitigate excessive ground forces while allowing a patient to maintain normal gait function. The system may also be adapted to address a variety of orthopedic remedial and therapeutic issues. These are other embodiments of the system and method in accordance with the invention will be described in detail herein below.

BRIEF DESCRIPTION OF THE DRAWINGS

For a better understanding of the invention, and to show how the same may be carried into effect, reference will now be made, by way of example, to the accompanying drawings. Those of skill in the art will appreciate that the FIGS. are not drawn to scales and various elements may be shorter or longer than as depicted or positioned higher or lower than as depicted.

DETAILED DESCRIPTION OF THE INVENTION

Figure 1:
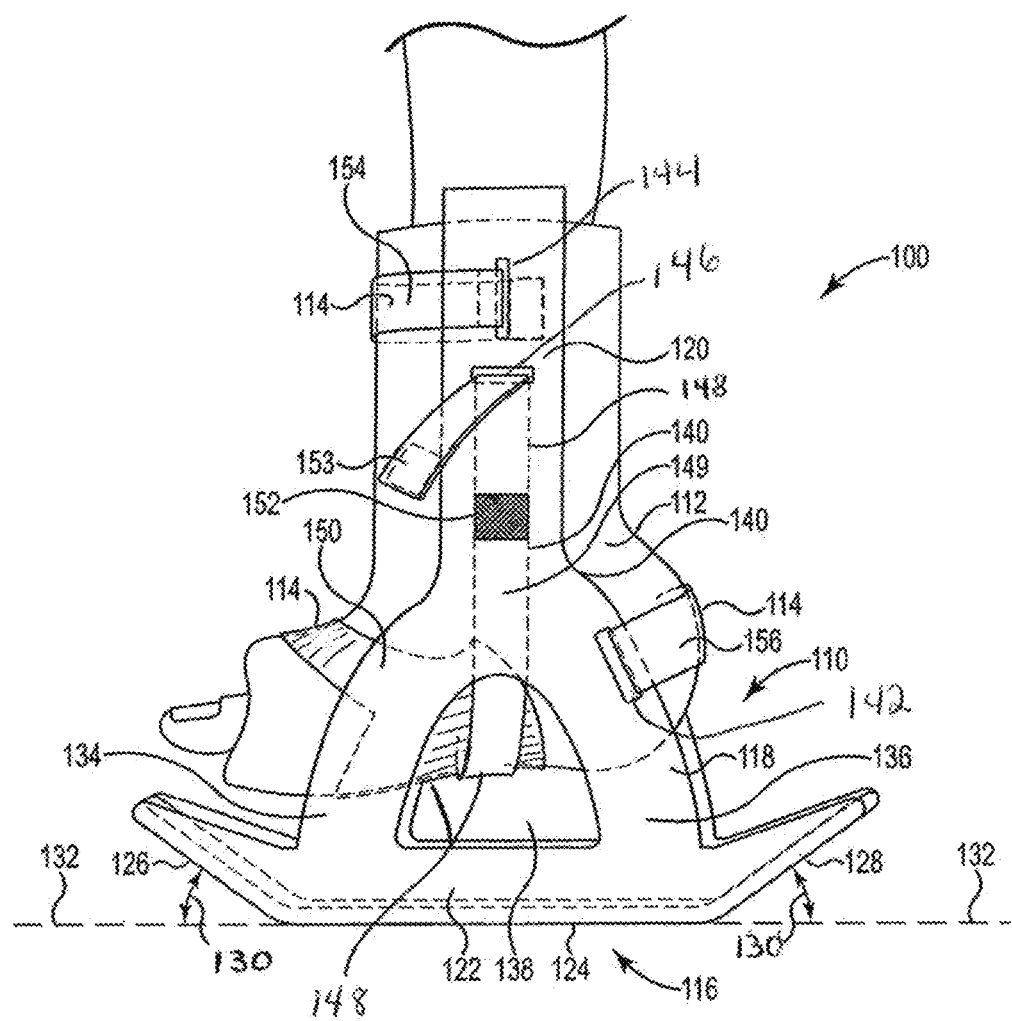
FIG. 1 is a side elevational view of an aspect of the invention shown on the lower extremity in a weight-bearing position.

Referring now to FIG. 1 a weighted aspect of the swing walker or suspension walker in accordance with the invention is illustrated. The swing walker depicted in FIG. 1 mitigates the impact forces subjected upon the foot if a patient is required to walk in a cast or a soft boot cam walker type construction. The swing walker 100 in accordance with a first aspect of the invention broadly includes a rocker base 110, a boot 112 and a plurality of straps 114.

Rocker base 110 includes rocker base sole 116 operably coupled to medial (not shown) and lateral yoke portions 118, each of which is coupled to medial (not shown) and lateral extension legs 120 extending from the yoke portion 118. The rocker base sole 116 includes a rocker base 122 that includes a substantially flat, weight bearing surface portion 124 for contacting the ground and first and second end portions 126, 128 that extend upwardly to form an acute angle 130 with the ground 132. First and second end portions 126, 128 may be made from a material that is resilient to allow them to dynamically deform during the gait cycle. Suitable materials that may be utilized include plastics, polymers and resilient metals. Weight bearing surface portion 124 may also be made from a material that is resilient to allow it to dynamically deform during the gait cycle. Suitable materials that may be utilized to construct rocker base sole 116 include polyolefin; polypropylene, open and closed cell foams and graphites. Yoke 118 and extension legs 120 may be made from rigid or semi-rigid materials such as plastics known to those of skill in the art.

Medial (not shown) and lateral yokes 118 take the shape of an upside down Y in cross section. Thus each of medial and lateral yokes 118 include distal and proximal arms 134, 136 defining an aperture therethrough. Distal and proximal arms 134, 136 may be integrally formed with rocker base sole 116 but be comprised of a different material construct. Alternatively, distal and proximal arms 134, 136 may be non-integrally formed with rocker base sole 116. Distal and proximal arms 134, 136 converge at an apex 140 to form extension leg 120. Proximal arm may define a first slot 142 therethrough for one of the plurality of straps 114 designed for use with the swing walker 100 in accordance with the invention.

Medial (not shown) and lateral extension legs 120 extends axially from apex 140 and defines an upper slot 144 and a mid-slot 146 therethrough for receiving two of said plurality of straps 114 designed for use with the swing walker 100 in accordance with the invention.

Inner boot 112 may be constructed of hard or soft plastics known to those of skill in the art and is suspended by a resilient yoke strap 148 including a front portion 150 that fits over the dorsum of the patient's foot and up underneath the planter surface of the arch. Resilient yoke strap 148 includes medial (not shown) and lateral portions 149 that are integrally or non-integrally formed with front portion 150. Medial and lateral portions 149 extend up the inside of extension legs 120 and exit through mid-slot 146 in the extension leg 120 and then is tractionable or tensionable by pulling down and fastening it to a fastener 152 located on the outside of extension leg 120. Fastener 152 may comprise Velcro and have a corresponding mating piece 153 on strap 148. Thus, resilient yoke strap 148 may be tensioned via fasteners 152, 153 to allow the inner boot 112 to be suspended off the weight bearing surface 124 or plane of support of the rocker base sole 116.

A second strap 154 runs anteriorly from side to side around the front portion of the boot at an upper edge. Second strap 154 prevents forward excursion of the inner boot 114 inside the swing walker. A third strap positioned through first slot 142 in the proximal arm 136 of yoke 118 provides posterior support behind and slightly above the heel and is designed to prevent excessive posterior excursion of the inner boot 112. When a patient inserts his foot in the swing walker 100 and weight bears in the construct, it creates tension on the flexible yoke strap 148 which may be operably coupled to and tension second and third straps 154, 156 to allow for a centering effect that holds the inner boot 112 more centrally located and stable during gait. Thus, when the patient propels during the normal gait cycle, there would not be quite as much free excursion or motion of the foot.

The basic premise of the swing walker in accordance with the invention including different aspects of the invention as disclosed herein is that the rocker base 110, which is a common component to all aspects of the invention, provides stability during the gait cycle allowing the foot excursion to move forward to load and suspend as it moves posteriorly and to swing up posteriorly providing different levels of support at heel strike, mid-stride and toe off based on the positioning of the leg during the gait cycle.

Figure 2:
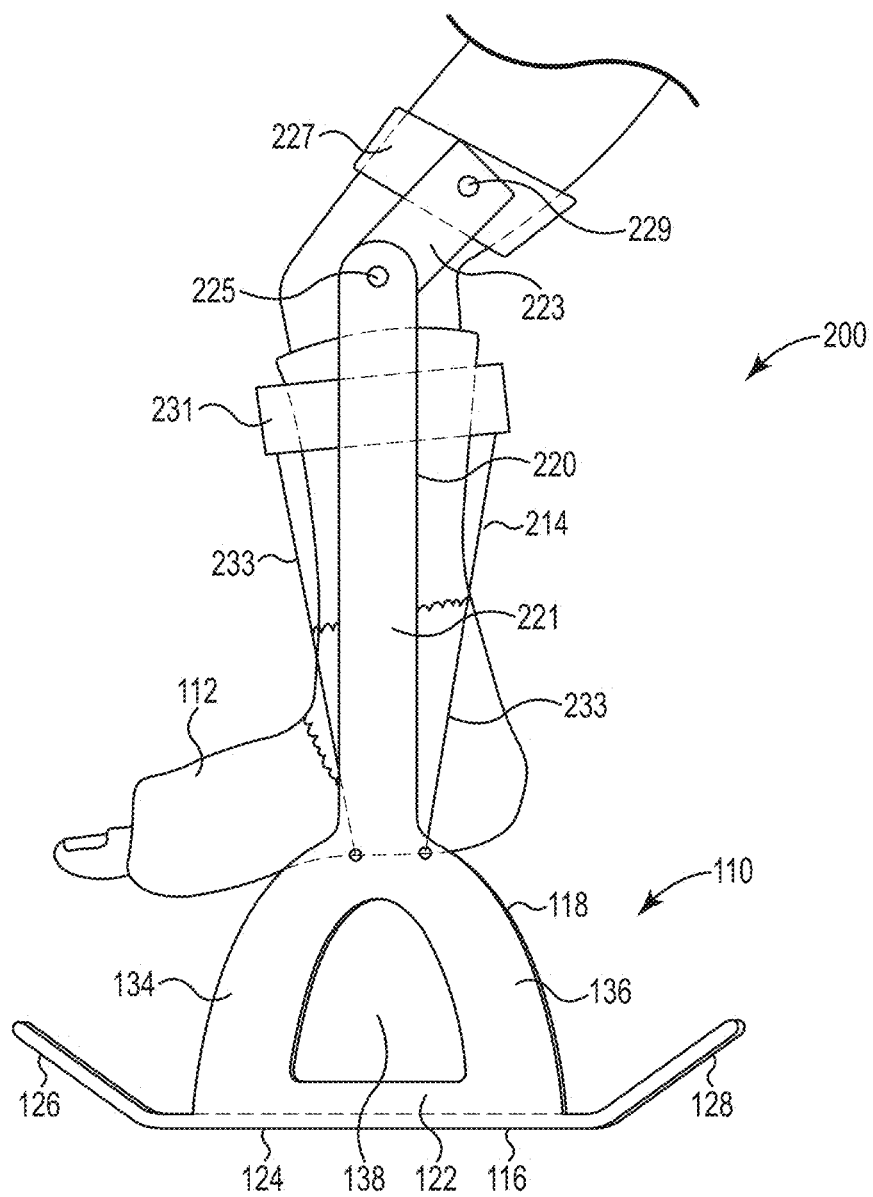
FIG. 2 is a side elevational view of an aspect of an unweighting invention shown functionally attached to the thigh with a an above-the-knee collar.

Turning now to FIG. 2 a further aspect of the swing walker 200 or suspension walker in accordance with the invention is illustrated. Components that are similar to the swing walker depicted in FIG. 1 are labeled with like numerals. The swing walker 200 in accordance with a further aspect of the invention comprises an unweighting swing walker and broadly includes a rocker base 110; boot 112; and cable system 214.

Rocker base 110 includes rocker base sole 116 operably coupled to medial (not shown) and lateral yoke portions 118, each of which is coupled to medial (not shown) and lateral double extension legs 220 extending from the yoke portion 118. The rocker base sole 116 includes a rocker base 122 that includes a substantially flat, weight bearing surface portion 124 for contacting the ground and first and second end portions 126, 128 that extend upwardly to form an acute angle 130 with the ground 132. First and second end portions 126, 128 may be made from a material that is resilient to allow them to dynamically deform during the gait cycle. Suitable materials that may be utilized include plastics, polymers and resilient metals. Weight bearing surface portion 124 may also be made from a material that is resilient to allow it to dynamically deform during the gait cycle. Suitable materials that may be utilized to construct rocker base sole 116 include polyolefin; polypropylene, open and closed cell foams and graphites. Yoke 118 and double extension legs 220 may be made from rigid or semi-rigid materials such as plastics known to those of skill in the art.

Medial (not shown) and lateral yokes 118 take the shape of an upside down Y in cross section. Thus each of medial and lateral yokes 118 include distal and proximal arms 134, 136 defining an aperture therethrough. Distal and proximal arms 134, 136 may be integrally formed with rocker base sole 116 but may be comprised of a different material construct. Alternatively, distal and proximal arms 134, 136 may be non-integrally formed with rocker base sole 116. Distal and proximal arms 134, 136 converge at an apex 140 to form medial (not shown) and lateral double extension legs 220. Double extension legs 220 include a distal extension leg 221 and a proximal extension leg 223. Distal and proximal extension legs 221, 223 are hingedly coupled together at first hinge axis 225. As those of skill in the art will appreciate, first hinge axis 225 is aligned with the rotational axis of the knee. A second end of proximal extension leg 225 is hingedly coupled to an above the knee collar 227 at second hinge axis 229. Above the knee collar 227 may totally or partially circumferentially surround the patient's leg and may be operably coupled to third hinge axis 222.

Inner boot 112 may be constructed of hard or soft plastics known to those of skill in the art and is suspended by cable system 214. Cable system 214 broadly includes a below the knee suspension collar 231 operably coupled to a plurality of cables 233. Below the knee suspension collar 231 may totally or partially circumferentially surround the patient's leg and is operably coupled to distal extension leg 221 at hinge axis 222. As those of skill in the art will appreciate, cables 233 may have variable attachment points on boot 112 such as the heel of the foot, at mid-foot (as shown) and other points. Inner boot 112 may be constructed of hard or soft plastics known to those of skill in the art.

As will be appreciated by those of skill in the art, the swing walker in accordance with a second aspect of the invention allows for additional unweighting other than just shock absorption. The swing walker in accordance with a second aspect of the invention decreases the impact force that is vertical and posterior or sheering at the heel upon impact during the gait cycle. The swing walker depicted in FIG. 2 allows for additional unweighting of the foot at above the knee suspension collar 227.

The below the knee collar 231 acts as a suspension collar for cables 233. Cables 233 may be coupled to the inner boot 112 which could be segmented to weight different segments of the forefoot, mid-foot, heel, lower leg, and upper leg to transmit the pressures of weight bearing suspension to a particular area.

For example, if a patient had a heel ulcer it would be desirable to weight the leg components at the mid-foot or forefoot with the cables 233 instead of the heel. The unweighting component comprises the below the knee collar 231 attached at the hinge axis 222 and suspending the segment attached by the cables.

Thus depending upon the desired pathology suspension collars may be coupled at various levels to various areas within the internal cast to allow for free swinging range of motion during gait. At heel strike the foot would be anterior to the vertical extension legs and would start to swing posteriorly and as it goes from a set down to pickup position, different cables from different suspension collars or locations would weight, load and unweight sequentially to allow for a continued level of support throughout the gait cycle. So certain cables for instance in this position right at toe off when this is about to be picked up or unweighted, the foot has already swung posteriorly and all the weight is really coming down from either above knee or below knee suspension collar and the cables are all loaded. On the patellar surface the cables are relatively unloaded to the leg or foot. However, because of the position of the leg as it passes the extension arm and the patellar surface during gait and because it is parallel to the ground, the system loads. Those of skill in the art will appreciate that the collars described herein may be constructed of known rigid, semi-rigid or resilient materials.

Figure 3:
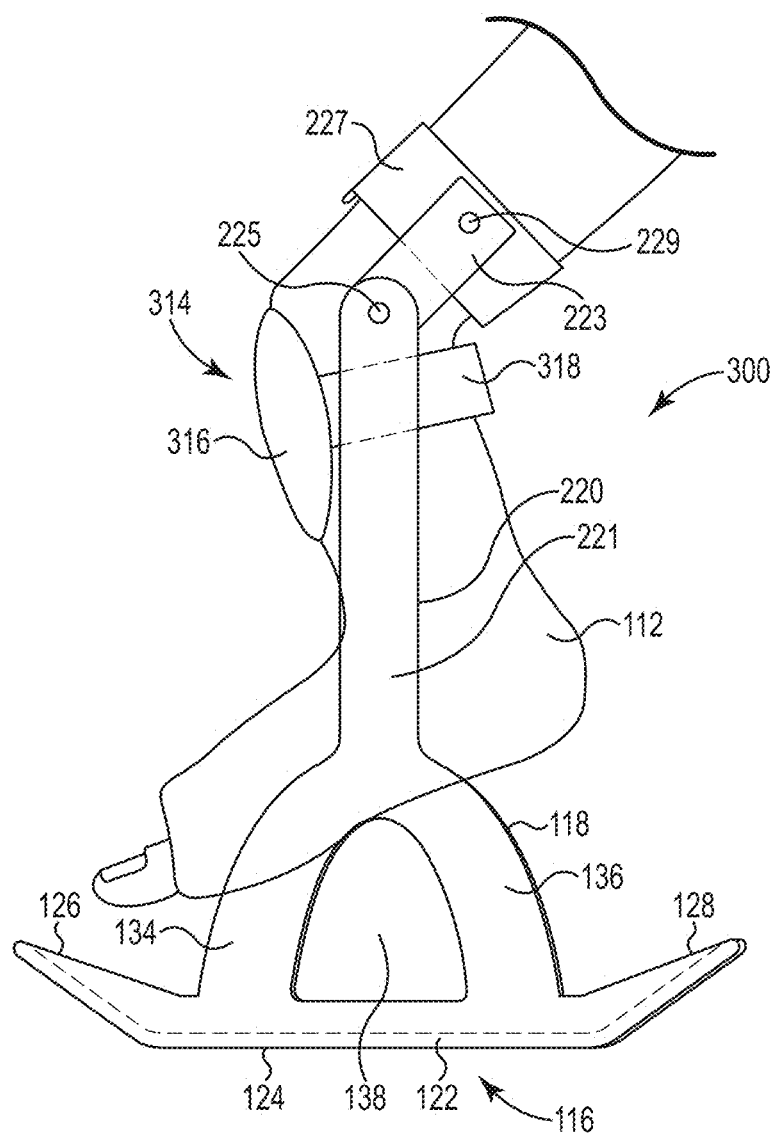
FIG. 3 is a side elevational view of an aspect of an unweighting invention similar to FIG. 2 except including a patellar suspension system.

Referring now to FIG. 3 a third aspect of a swing walker 300 in accordance with the invention is shown. Components that are similar to the swing walker depicted in FIGS. 1 and 2 are labeled with like numerals. The swing walker 300 in accordance with a third aspect of the invention comprises an unweighting swing walker and broadly includes a rocker base 110; inner boot 112; and patellar suspension system 314.

Rocker base 110 includes rocker base sole 116 operably coupled to medial (not shown) and lateral yoke portions 118, each of which is coupled to medial (not shown) and lateral double extension legs 220 extending from the yoke portion 118. The rocker base sole 116 includes a rocker base 122 that includes a substantially flat, weight bearing surface portion 124 for contacting the ground and first and second end portions 126, 128 that extend upwardly to form an acute angle 130 with the ground 132. First and second end portions 126, 128 may be made from a material that is resilient to allow them to dynamically deform during the gait cycle. Suitable materials that may be utilized include plastics, polymers and resilient metals. Weight bearing surface portion 124 may also be made from a material that is resilient to allow it to dynamically deform during the gait cycle. Suitable materials that may be utilized to construct rocker base sole 116 include polyolefin; polypropylene, open and closed cell foams and graphites. Yoke 118 and double extension legs 220 may be made from rigid or semi-rigid materials such as plastics known to those of skill in the art.

Medial (not shown) and lateral yokes 118 take the shape of an upside down Y in cross section. Thus each of medial and lateral yokes 118 include distal and proximal arms 134, 136 defining an aperture therethrough. Distal and proximal arms 134, 136 may be integrally formed with rocker base sole 116 but may be comprised of a different material construct. Alternatively, distal and proximal arms 134, 136 may be non-integrally formed with rocker base sole 116. Distal and proximal arms 134, 136 converge at an apex 140 to form medial (not shown) and lateral double extension legs 220.

Double extension legs 220 include a distal extension leg 221 and a proximal extension leg 223. Distal and proximal extension legs 221, 223 are hingedly coupled together at first hinge axis 225. As those of skill in the art will appreciate, first hinge axis 225 is aligned with the knee at the rotational axis of the knee. A second end of proximal extension leg 225 is fixedly coupled to above the knee collar 227.

Turning now to the above the knee patellar suspension system 670, the system broadly includes an above the knee collar 227, plurality of cables 374 and knee support 316. Plurality of cables 374 are coupled to the knee support 316 at a first end thereof and coupled at a second end to above the knee collar 227. Each coupling of cables 374 to knee support 316 are at different coupling locations on knee support 316 and each coupling of the second end of cables 374 to the above the knee collar 227 are at various locations on the above the knee collar 227. Those of skill in the art will appreciate that plurality of cables 374 may comprise wires, straps, tethers, filaments and the like and may be constructed from flexible, resilient or semi-rigid materials. Above the knee collar 227 may partially or totally circumferentially surround the patient's leg.

Strap 318 assists in securing knee support 316 to the leg at a position below the knee. Strap 318 may be constructed of resilient or non-resilient fabric or other materials known to those of skill in the art.

Figure 4:
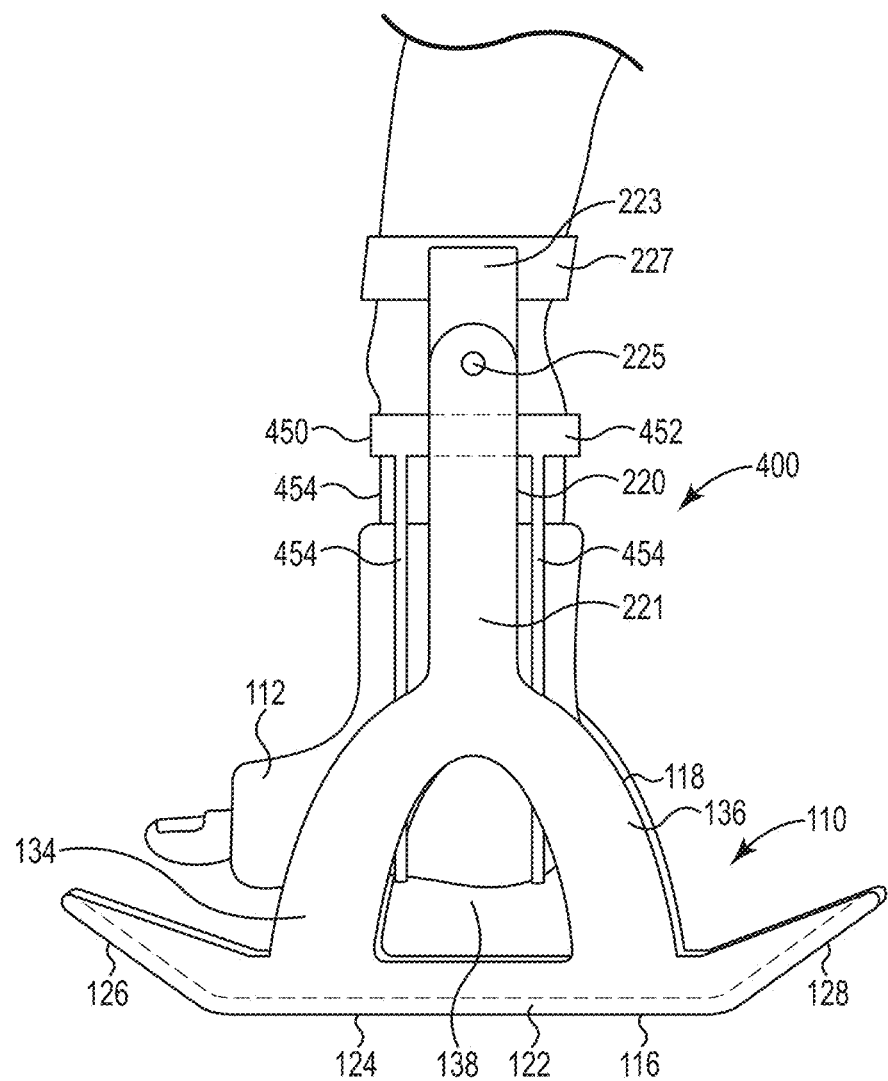
FIG. 4 is a side elevational view of a further aspect of an unweighting invention and a variation of the embodiment shown in FIG. 2.

Referring now to FIG. 4 an unweighting swing walker with a below the knee suspension system is shown 400. The weighted swing walker with below the knee suspension system 400 broadly includes rocker base 110, below the knee suspension system 450 and above the knee collar 227. Rocker base 110 is substantially similar to previously described embodiments and includes rocker base sole 116 operably coupled to medial (not shown) and lateral yoke portions 118, each of which is coupled to medial (not shown) and lateral double extension legs 220 extending from the yoke portion 118. The rocker base sole 116 includes a rocker base 122 that includes a substantially flat, weight bearing surface portion 124 for contacting the ground and first and second end portions 126, 128 that extend upwardly to form an acute angle 130 with the ground 132. First and second end portions 126, 128 may be made from a material that is resilient to allow them to dynamically deform during the gait cycle. Suitable materials that may be utilized include plastics, polymers and resilient metals. Weight bearing surface portion 124 may also be made from a material that is resilient to allow it to dynamically deform during the gait cycle. Suitable materials that may be utilized to construct rocker base sole 116 include polyolefin; polypropylene, open and closed cell foams and graphites. Yoke 118 and double extension legs 221 may be made from rigid or semi-rigid materials such as plastics known to those of skill in the art.

Medial (not shown) and lateral yokes 118 take the shape of an upside down Y in cross section. Thus each of medial and lateral yokes 118 include distal and proximal arms 134, 136 defining an aperture therethrough. Distal and proximal arms 134, 136 may be integrally formed with rocker base sole 116 but may be comprised of a different material construct. Alternatively, distal and proximal arms 134, 136 may be non-integrally formed with rocker base sole 116. Distal and proximal arms 134, 136 converge at an apex 140 to form medial (not shown) and lateral double extension legs 220.

Double extension legs 220 include a distal extension leg 221 and a proximal extension leg 223. Distal and proximal extension legs 221, 223 are hingedly coupled together at first hinge axis 225. As those of skill in the art will appreciate, first hinge axis 225 is aligned with the knee at the rotational axis of the knee. Proximal extension leg 225 is fixedly coupled to above the knee collar 227. Distal extension leg 221 is fixedly coupled to below the knee collar 452.

Below the knee suspension system 450 operates to suspend boot 112 and includes below the knee collar 452 operably coupled to a plurality of cables 454. Below the knee collar 452 circumferentially surrounds the patient's leg below the knee. As those of skill in the art will appreciate, cables 454 may comprise wires, straps, tethers, filaments and the like and may be flexible, resilient or semi-rigid. Cables 454 act to suspend boot 112 to eliminate impact forces with the ground and to allow for free range of motion of the foot during the gait cycle.

Figure 5:
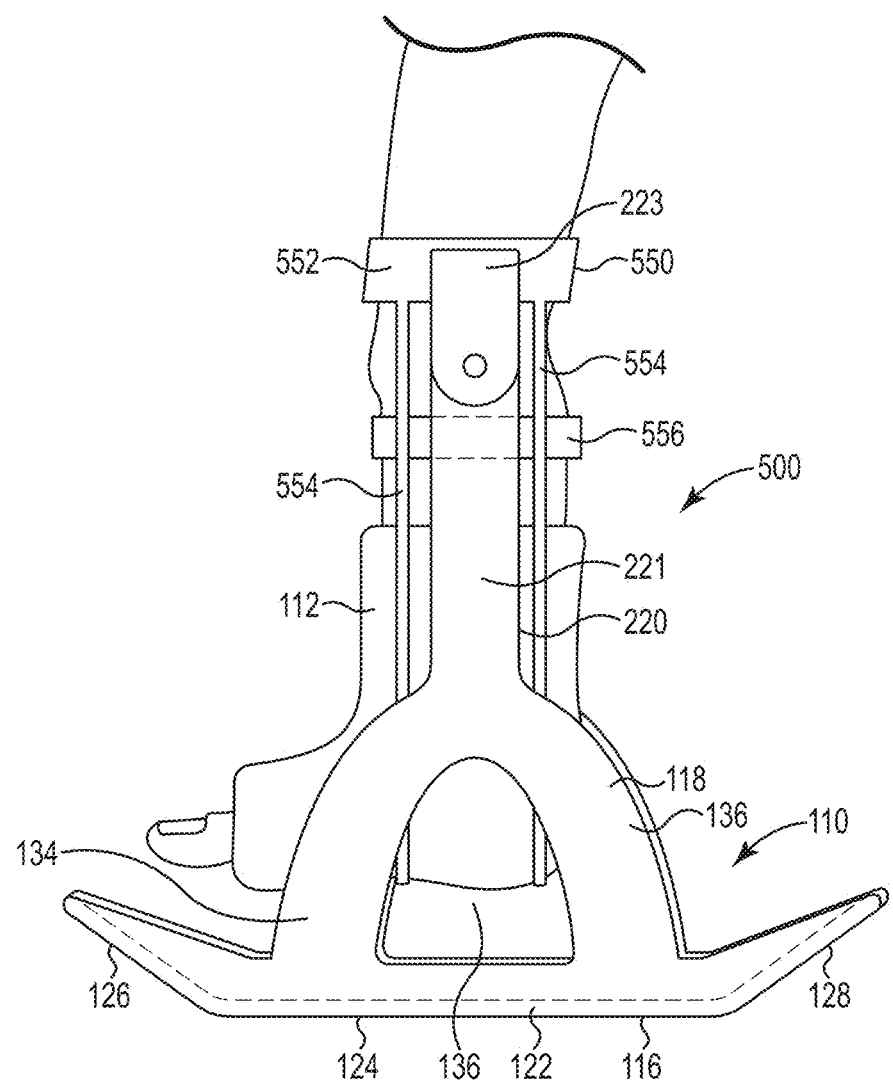
FIG. 5 is a side elevational view of a further aspect of an unweighting invention and a variation of the embodiment shown in FIG. 2.

Referring now to FIG. 5 an alternative embodiment of a weighted swing walker in accordance with the invention 500 is shown. FIG. 5 is substantially similar to the embodiment shown in FIG. 4 except an above the knee suspension system 550 is used. The weighted swing walker with above the knee suspension system 550 broadly includes rocker base 110, above the knee suspension system 450 and above the knee collar 414. Rocker base 110 is substantially similar to previously described embodiments and includes rocker base sole 116 operably coupled to medial (not shown) and lateral yoke portions 118, each of which is coupled to medial (not shown) and lateral double extension legs 220 extending from the yoke portion 118. The rocker base sole 116 includes a rocker base 122 that includes a substantially flat, weight bearing surface portion 124 for contacting the ground and first and second end portions 126, 128 that extend upwardly to form an acute angle 130 with the ground 132. First and second end portions 126, 128 may be made from a material that is resilient to allow them to dynamically deform during the gait cycle. Suitable materials that may be utilized include plastics, polymers and resilient metals. Weight bearing surface portion 124 may also be made from a material that is resilient to allow it to dynamically deform during the gait cycle. Suitable materials that may be utilized to construct rocker base sole 116 include polyolefin; polypropylene, open and closed cell foams and graphites. Yoke 118 and double extension legs 221 may be made from rigid or semi-rigid materials such as plastics known to those of skill in the art.

Medial (not shown) and lateral yokes 118 take the shape of an upside down Y in cross section. Thus each of medial and lateral yokes 118 include distal and proximal arms 134, 136 defining an aperture therethrough. Distal and proximal arms 134, 136 may be integrally formed with rocker base sole 116 but may be comprised of a different material construct. Alternatively, distal and proximal arms 134, 136 may be non-integrally formed with rocker base sole 116. Distal and proximal arms 134, 136 converge at an apex 140 to form medial (not shown) and lateral double extension legs 220.

Double extension legs 220 include a distal extension leg 221 and a proximal extension leg 223. Distal and proximal extension legs 221, 223 are hingedly coupled together at first hinge axis 225. As those of skill in the art will appreciate, first hinge axis 225 is aligned with the knee at the rotational axis of the knee. Proximal extension leg 225 is fixedly coupled to above the knee collar 552. Distal extension leg 221 is fixedly coupled to below the knee collar 556. Both above the knee collar 552 and below the knee collar 556 circumferentially surround the patient's leg.

Above the knee suspension system 550 operates to suspend boot 112 and includes above the knee collar 552 operably coupled to a plurality of cables 554. As those of skill in the art will appreciate, cables 554 may comprise wires, straps, tethers, filaments and the like and may be flexible, resilient or semi-rigid. Cables 554 act to suspend boot 112 to eliminate impact forces with the ground and to allow for free range of motion of the foot during the gait cycle.

Figure 6:
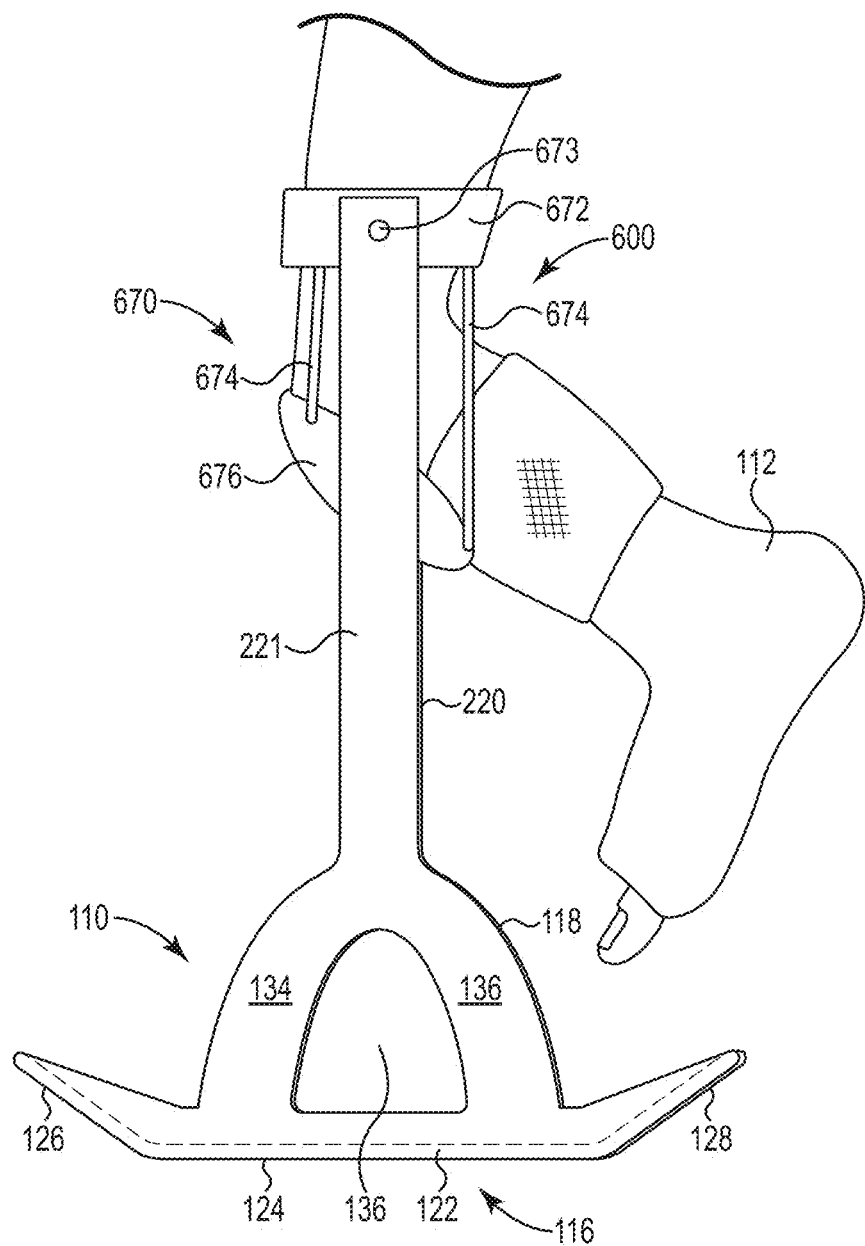
FIG. 6 is a side elevational view of a further aspect of the invention similar to FIG. 3 except it is unhinged at the rotational axis of the knee.

Referring now to FIG. 6 an embodiment of an unweighting swing walker 600 similar to the embodiment in FIG. 3 is shown. Like elements are labeled with like numerals. The swing walker in accordance with the invention depicted in FIG. 6 broadly includes a rocker base 110; a boot 112 and an above the knee patellar suspension system 670. As the rocker base is substantially identical to previous embodiments further explanation will not be provided.

Turning now to the above the knee patellar suspension system 670, the system broadly includes an above the knee collar 672, plurality of cables 674 and knee support 676. Plurality of cables 674 are coupled to the knee support 676 at a first end thereof and coupled at a second end to above the knee collar 672 along the longitudinal axis of the proximal extension arm 221. Each coupling of cables 674 to knee support 676 are at different coupling locations on knee support 676 and each coupling of the second end of cables 674 to the above the knee collar 672 are at various locations on the above the knee collar 672. Those of skill in the art will appreciate that plurality of cables 674 may comprise wires, straps, tethers, filaments and the like and may be constructed from flexible, resilient or semi-rigid materials. Above the knee collar 672 totally or partially circumferentially surrounds the patient's thigh.

Proximal extension arm 221 of the rocker base 110 is hingedly coupled to above the knee collar 672 at point 673. Those of skill in the art will appreciate that the above the knee patellar suspension system provide a weight bearing surface that allows for unweighting at the patellar surface and the anterior knee and superior shin. The above the knee patellar suspension system thus acts to suspend the leg at the at the patellar surface and the anterior knee and superior shin depending on the type of foot pathology that is being treated and the desired correction and allows for free swinging range of motion during gait.

Figure 7:
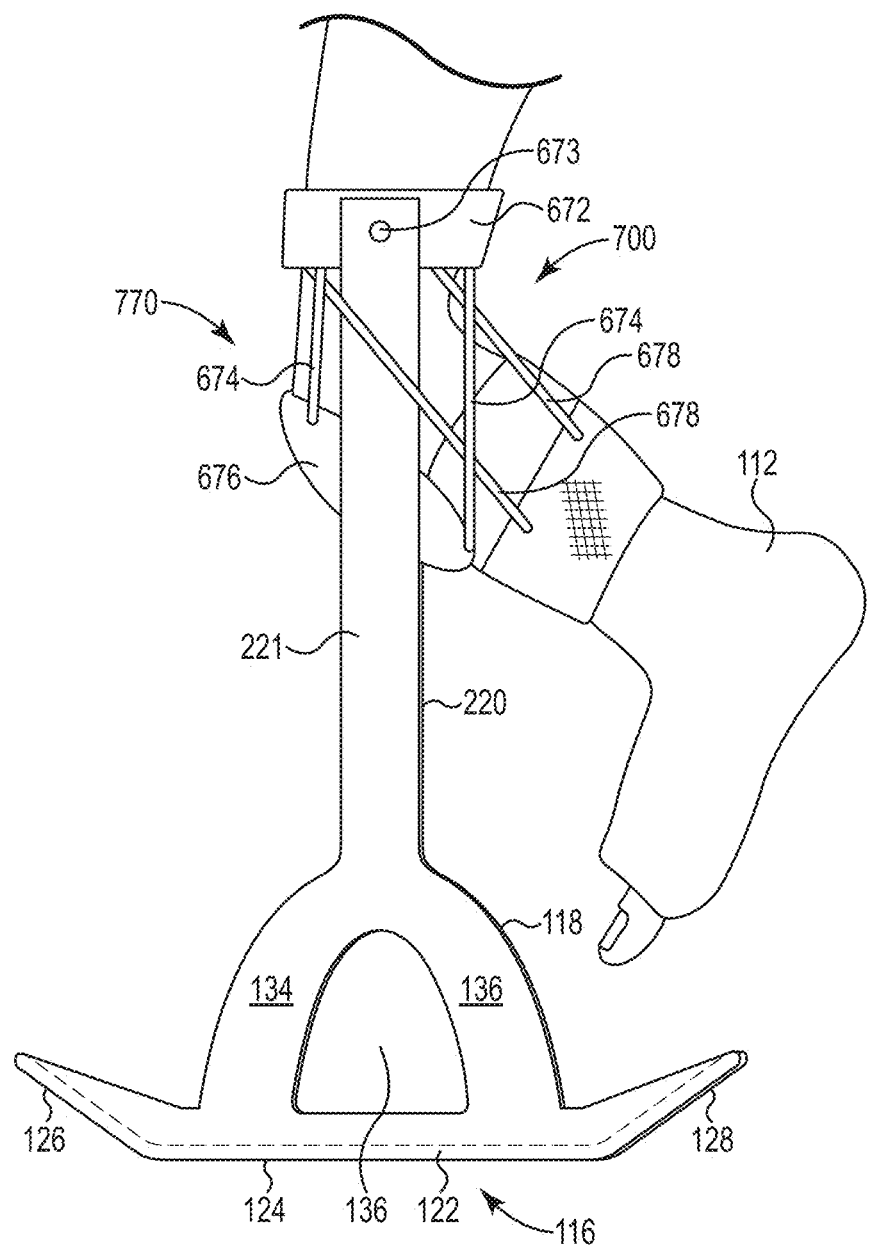
FIG. 7 is a side elevational view of a further aspect of an unweighting invention.

Turning now to FIG. 7 a modified version of the embodiment shown in FIG. 6 is depicted. FIG. 7 depicts an unweighting swing walker with an above the knee patellar support suspension system which is partially unweighted by diagonal suspension with a second set of cables 678 from above the knee collar to inner boot 112.

Above the knee patellar support suspension system 700 includes a second plurality of cables 678 that are coupled at a first end thereof the boot 112 and to above the knee collar 672 at a second end thereof. Cables 678 run in a diagonal attachment pattern from above the knee collar 672 to boot 112. As those of skill in the art will appreciate because the knee patellar support suspension system 700 does not hinge at the knee the leg does not swing through the channel created between extension arms 220, 221. Thus, the leg is held in a fixed position while still allowing the patient to ambulate through the gait cycle.

Figure 8:
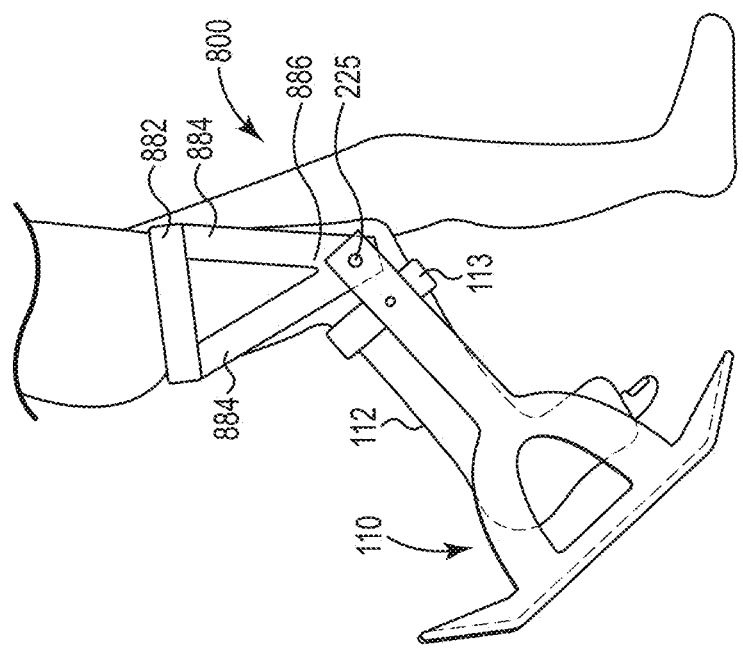
FIG. 8 is a side elevational view of further aspect of an unweighting invention attached to a leg in an initial step position of stride.
Figure 9:
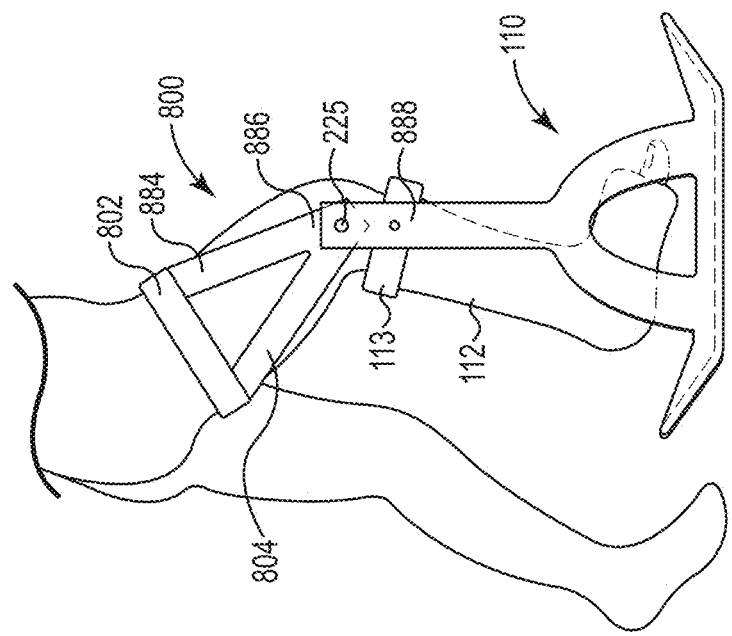
FIG. 9 is a side elevational view of the embodiment of FIG. 8 shown at the end of stride position commonly known as "toe-off"

Turning now to FIGS. 8 and 9 a side elevational view of a thigh walker 800 in accordance with the invention showing the invention attached to the upper thigh of a patient with the leg in an initial step position of stride (FIG. 8) and shown at the end of stride (FIG. 9) during the gait cycle. As can be seen from the FIGS. the thigh walker include rocker base 110, which is substantially similar to previous embodiments, boot 112 with upper boot collar 113 and thigh suspension system 880.

Thigh suspension system 880 includes upper collar 882 and V-shaped legs 884 that join at apex 886. Those of skill in the art will appreciate that upper collar 882 may totally or partially circumferentially surround the patient's thigh and may be lower on the thigh than as shown. Apex 886 is hingedly coupled to single extension leg 888 of the rocker base system 110. Those of skill in the art will appreciate that single extension leg 888 is hingedly coupled by hinge joint 225 to apex at the rotational axis point 225 of the knee as in previously disclosed embodiments. Thus, the lower leg can move through the channel created by upright extension legs 888 but movement is constrained by hinge joint 225.

Figures 10, 11:
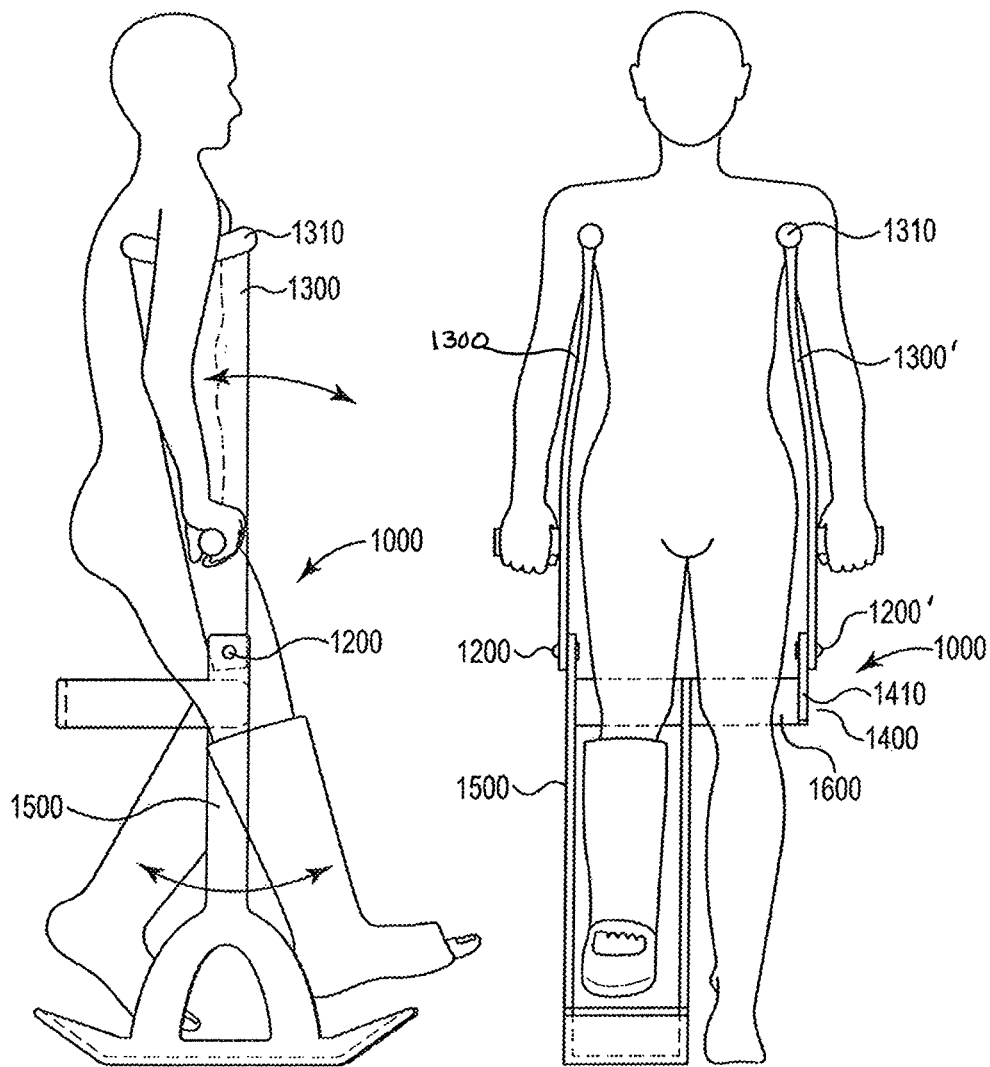
FIG. 10 is a side elevational view of a further aspect of the invention showing functional range of motion thereof.
FIG. 11 is a front elevational view of FIG. 10.

Turning now to FIGS. 10 and 11 a further aspect of the present invention is shown. The crutch walker 1000 in accordance with the invention is a progression for the swing walker that adds stability during the gait cycle. When the crutch walker 1000 is picked up and placed down and the leg is swinging and moving through it, the stabilization is provided by right and left arm components 1300, 1300' that fits between the torso and the shoulder underneath the arm. The arm components 1300, 1300' includes right and left hinge component 1200, 1200' that operably couples the arm components 1300, 1300' with the rocker base system 110. The hinge components 1200, 1200' allows the patient to actually rock posteriorly when the crutch walker 1000 is set down in front of them and hinge and rotate anteriorly as the leg swings posteriorly. The crutch then moves anteriorly so it provides for a counterbalance during gate for stability. The crutch walker includes a right side 1400 and a left side 1500. On the right side, the crutch walker includes the arm component 1300, hinge component 1200 and rocker base system 1500. The left side 1400 includes the arm component 1300' and hinge component 1200' with a short extension arm 1410 hingedly coupled thereto. Short extension arm 1410 is coupled to rocker base system 1500 by bar 1600. Hinges 1200, 1200' are at or above the level of the rotational knee axis. Bar 1600 provides stability that allows the patient to use the same type of crutch component on the right side but the other leg could walk free without being inside a swing walker for stability. The crutch walker in accordance with the invention is an advancement over prior art crutch systems because the crutches do not need to be splayed out at an angle and attack the ground at an angle potentially causing the crutch to kick out or slip especially in situations involving ice and snow. The crutch walker 1000 in accordance with the invention traps and stabilizes the pathological extremity in a stable support that does not allow it to be impacted from either side; allows for multiple levels of unweighting to occur; and allows for free swinging or motion during the gait cycle which facilitates more normal function, less disuse and atrophy of the extremity, and improves blood flow.

Those of skill in the art will appreciate that the crutch walker depicted in FIGS. 10 and 11 does not need to be a "full" crutch with underarm support 1310. Rather arm component 1300 may comprise a single element that may be coupled to an above-the elbow position and hingedly attached to the upright support element.

Those of skill in the art will also appreciate that the disclosed embodiments in accordance with the invention are designed to accommodate numerous modifications as hereinbefore described. Thus, although the present invention has been described with reference to certain embodiments, those of ordinary skill in the art will recognize that changes may be made in form and detail without departing from the spirit and scope of the invention.

I claim:

1. A suspension crutch walker for use by a user on a surface such as a ground comprising:
   an inner boot for holding a user's foot;
   an integrally formed rocker base having a front portion offset by an acute angle from the ground, a back portion offset by an acute angle from the ground and a substantially flat, weight bearing surface middle portion;
   Y-shaped medial and lateral yoke portions each including distal and proximal arms defining apertures therethrough, the distal and proximal arms each coupled to said rocker base;
   a medial extension leg operably coupled to said medial yoke portion and a lateral extension leg operably coupled to said lateral yoke portions, said medial extension leg and said lateral extension leg extending axially upwardly from said medial yoke portion and said lateral yoke portion, respectively;

a right and left elongate arm component having first and second ends, each of said right and left elongate arm components having an underarm support at the first end thereof positionable under a right and left armpit of the user; and a first hinge operably coupled to one of said right or left elongate arm components and said lateral extension leg.

2. The suspension crutch walker of claim 1 further comprising a lateral bar coupled to said lateral extension leg, said lateral bar extending horizontally across and behind a right and left leg of the user.

3. The suspension crutch walker of claim 2 further comprising an extension arm having first and second ends, said first end hingedly coupled to the second end of at least one of said right or left elongate arm components.

4. The suspension crutch walker of claim 3 wherein said second end of said extension arm is coupled to said lateral bar.

* * * * *